United States Patent
Schatz

[11] Patent Number: 5,868,753
[45] Date of Patent: Feb. 9, 1999

[54] STENT RETRIEVAL CATHETER

[76] Inventor: Richard A. Schatz, P.O. Box 8517, Rancho Santa Fe, Calif. 92067

[21] Appl. No.: 557,723

[22] Filed: Nov. 13, 1995

[51] Int. Cl.$^6$ ..................................................... A61F 11/00
[52] U.S. Cl. ........................ 606/108; 606/192; 606/195; 606/198; 606/194
[58] Field of Search .................... 606/108, 194, 606/198, 192, 127, 195

[56] References Cited

U.S. PATENT DOCUMENTS

| | | | |
|---|---|---|---|
| 3,421,509 | 1/1969 | Fiore | 606/108 |
| 3,842,441 | 10/1974 | Kaiser . | |
| 4,140,126 | 2/1979 | Choudhury . | |
| 4,315,509 | 2/1982 | Smit . | |
| 4,434,797 | 3/1984 | Silander . | |
| 4,483,339 | 11/1984 | Gillis . | |
| 4,512,338 | 4/1985 | Balko et al. . | |
| 4,594,996 | 6/1986 | Ibrahim et al. | 128/1 R |
| 4,732,152 | 3/1988 | Wallsten et al. . | |
| 4,744,366 | 5/1988 | Jang | 606/194 |
| 4,800,882 | 1/1989 | Gianturco . | |
| 4,886,062 | 12/1989 | Wiktor . | |
| 4,907,336 | 3/1990 | Gianturco . | |
| 4,913,141 | 4/1990 | Hillstead . | |
| 4,921,478 | 5/1990 | Solano et al. | 604/53 |
| 4,932,959 | 6/1990 | Horzewski et al. | 606/194 |
| 5,026,377 | 6/1991 | Burton et al. | 606/108 |
| 5,053,013 | 10/1991 | Ensminger et al. . | |
| 5,156,596 | 10/1992 | Balbierz et al. . | |
| 5,330,482 | 7/1994 | Gibbs et al. | 606/113 |
| 5,334,208 | 8/1994 | Soehendra et al. | 606/108 |
| 5,409,495 | 4/1995 | Osborn | 606/108 |
| 5,411,507 | 5/1995 | Heckele | 606/108 |
| 5,464,408 | 11/1995 | Duc | 606/108 |
| 5,474,563 | 12/1995 | Myler et al. | 606/108 |
| 5,520,697 | 5/1996 | Lindenberg et al. | 606/108 |
| 5,549,615 | 8/1996 | Hocherl et al. | 606/108 |
| 5,624,450 | 4/1997 | Glastra | 606/198 |
| 5,628,754 | 5/1997 | Shevlin et al. | 606/108 |
| 5,653,684 | 8/1997 | Laptewicz et al. | 606/108 |
| 5,683,451 | 11/1997 | Lenker et al. | 606/198 |

FOREIGN PATENT DOCUMENTS

| | | |
|---|---|---|
| 0 274 846 A1 | 7/1988 | European Pat. Off. . |
| 2 104 673 | 3/1972 | Germany . |

*Primary Examiner*—Michael A. Brown
*Assistant Examiner*—Justine R. Yu
*Attorney, Agent, or Firm*—Crompton, Seager & Tufte, LLC

[57] ABSTRACT

A device and method for retrieving a stent from the vessel of a patient includes a catheter which is formed with a central lumen that defines a passageway having a diameter. A deformable distal tip is attached to the catheter to establish an extension of the passageway. In the operation of the device, the distal tip is initially maintained in a first configuration wherein the stent can be received into and through the passageway. While the distal tip is maintained in this first configuration, a portion of the stent to be retrieved is withdrawn into the passageway of the distal tip. The distal tip is then distended or deformed into a second configuration wherein the diameter of the passageway is reduced to grip the stent. The catheter and the gripped stent are then retrieved from the vessel of the patient.

10 Claims, 3 Drawing Sheets

STENT RETRIEVAL CATHETER

FIELD OF THE INVENTION

The present invention pertains generally to medical devices which are used in cardio-vascular surgery. More particularly, the present invention pertains to medical devices which are useful for deploying a stent into the vessel of a patient for the purpose of maintaining patency of the vessel. The present invention is particularly, but not exclusively useful for retrieving a stent from the vessel of a patient thus preventing stent dislodgement when it has been determined that delivery of the stent has, in some respect, been unsuccessful.

BACKGROUND OF THE INVENTION

Many kinds of stents are quite frequently used in cardio-vascular surgery for the purpose of providing a supporting structure for anatomical vessels. More specifically, stents are often placed at the site of a stenosis in a vessel to establish and maintain the patency of the vessel. This, of course, may be necessary in order to allow for the continued flow of blood through the vessel. Not surprisingly, the deployment and accurate placement of a stent in the vessel of a patient requires a great deal of skill.

As difficult as it may be to deploy and emplace a stent, the effort required to retrieve a misplaced stent can be equally as difficult, if not more so. To appreciate this, first consider how a stent is placed in a vessel such as an artery. Typically, the stent is deployed into the vessel of a patient with the stent mounted over the balloon of a balloon catheter. As so mounted, the stent is passed through a previously positioned guiding catheter and to the desired location in the vessel. Actual placement of the stent in the vessel is then accomplished by extending the stent and balloon catheter beyond the distal end of the guiding catheter where the balloon can then be inflated at the target site. This balloon inflation extends the stent and then separates the stent from the balloon upon balloon deflation. At this point, if, as sometimes can happen, trouble is encountered in delivering the stent to the target site prior to deployment, the stent should be retrieved. The retrieval of a stent from a body vessel necessarily requires the engagement of a retrieval instrument with the stent. Ideally, because the placement catheter is already in place, the stent can be withdrawn into the placement catheter and then removed from the vessel without stent dislodgement. Engagement of the placement catheter with the stent, however, can be troublesome. Specifically, during withdrawal of the stent into the placement catheter, it can happen that the stent snags on the catheter. Most often, this snagging occurs at or near the distal end of the placement catheter. Further, the problem can be aggravated by the presence of a relatively soft distal tip which is typically attached to the distal end of the catheter to reduce trauma to the patient.

Should the stent become snagged or the distal end of the catheter, the balloon, which has only the ability to expand the stent, will be of little value in retrieving the stent. On the other hand, the present invention recognizes that the placement catheter may, itself, be helpful in accomplishing the task of retrieving the stent.

In light of the above, it is an object of the present invention to provide a device for retrieving a stent from the vessel of a patient which can grip onto and hold the stent during its removal from the vessel. Yet another object of the present invention is to provide a device for retrieving a stent from the vessel of a patient which is simple to use, relatively easy to manufacture and comparatively cost effective.

SUMMARY OF THE INVENTION

A device for retrieving a misplaced stent from the vessel of a patient includes a catheter which is formed with a central lumen. This central lumen defines a passageway which is dimensioned with a diameter that initially allows the stent to pass through the passageway of the catheter for emplacement in a vessel when the stent is in a collapsed configuration. Importantly, the device also includes a soft distal tip that is attached to the distal end of the catheter.

In the preferred embodiment of the device for the present invention, the distal tip is formed with a chamber that is established between a relatively rigid outer wall and a relatively flexible inner wall. As oriented on the device, the flexible inner wall surrounds and defines a portion of the passageway. Relative to the inner wall, the outer wall is located outwardly and radially therefrom. Additionally, an inflation means is engageable with the catheter to connect the inflation means in fluid communication with the chamber in the distal tip via an inflation lumen in the catheter.

In an alternate embodiment of the device for the present invention, the distal tip is also formed with a compartment that is located distally from the chamber. With structure that is reversed but somewhat similar to that of the chamber, the compartment is established between a relatively flexible outer panel and a relatively rigid inner panel. Like the chamber, the compartment in the distal tip can be placed in fluid communication with the inflation means.

In the operation of the device of the present invention, the guiding catheter is initially positioned in the vessel of a patient for placement of a stent into the vessel. A balloon catheter is then provided, with the stent to be deployed, collapsed and positioned over the deflated balloon. The collapsed stent is then passed through the central lumen of the device and deployed into the vessel at the site where it is to support the vessel.

If, for some reason, the delivery of the stent is unsuccessful and the stent snags upon attempted withdrawal into the guiding catheter, the proximal end of the stent is withdrawn into that portion of the passageway which is surrounded by the distal tip until resistance is felt. The inflation means is then activated to inflate the chamber. With this inflation of the chamber, the relatively flexible inner wall distends. This, in turn, reduces the diameter of the passageway and causes the distal tip of the catheter to grip onto the stent. The device can then be withdrawn from the vessel along with the stent that is being gripped by its distal tip while the guiding wire remains in the body vessel.

To facilitate entry of the stent into the guiding catheter, as indicated above, the distal tip of the catheter can be further formed with a compartment which is located distally from the chamber. Inflation of this compartment by the inflation means distends the flexible outer panel of the compartment and causes the extreme distal portion of the distal tip to flare. This flaring facilitates withdrawal of the stent into the passageway of the catheter. This maneuver alone may allow complete stent retrieval. If the stent snags despite this, however, the chamber can then be inflated in the manner as indicated above, to grip the stent. In either case, the device with the gripped stent is then withdrawn from the patient.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENTS

Figure 1:
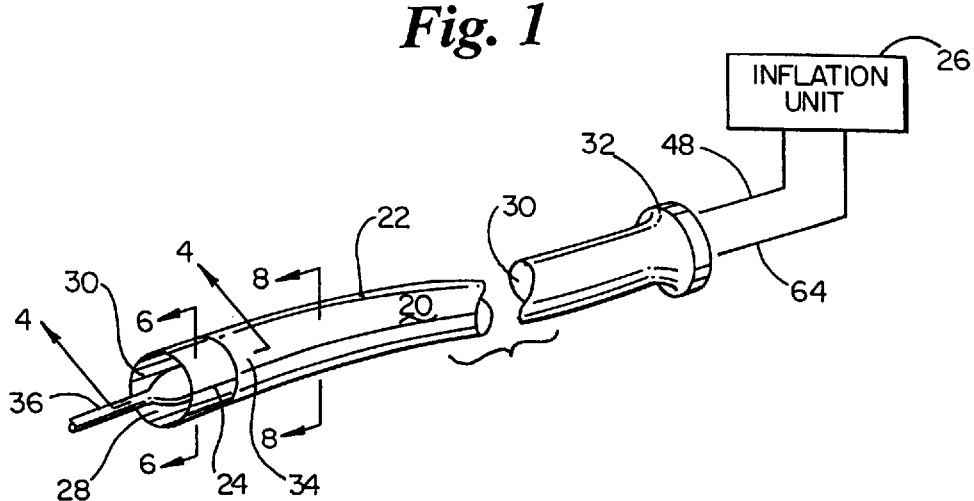
FIG. 1 is a perspective view of the device of the present invention.

Referring initially to FIG. 1, a device for retrieving a stent from the vessel of a patient is shown and is generally designated 20. As shown, the device 20 includes an elongated catheter 22 having a distal tip 24 which is attached thereto by any means well known in the pertinent art, such as by bonding. Additionally, the device 20 includes an inflation unit 26 which is engageable with the catheter 22 for purposes to be more fully disclosed below. To accomplish the intended tasks of the present invention, the catheter 22 is preferably made of a teflon duralin material and the distal tip 24 is made of a relatively elastic material such as latex. It will be appreciated by the skilled artesan, however, that other bio-compatible materials are suitable for the manufacture of the catheter 22 or the distal tip 24.

FIG. 1 also shows that the catheter 22 is formed with a central lumen 28 which creates a passageway 30. Though not shown in its entirety, it is to be understood that the passageway 30 extends the entire length of the catheter 22 from the proximal end 32 of catheter 22 to its distal end 34. As further indicated in FIG. 1, distal tip 24 is attached to this distal end 34 of catheter 22 and the passageway 30 extends from the catheter 22 through the (soft) distal tip 24.

Figure 2:
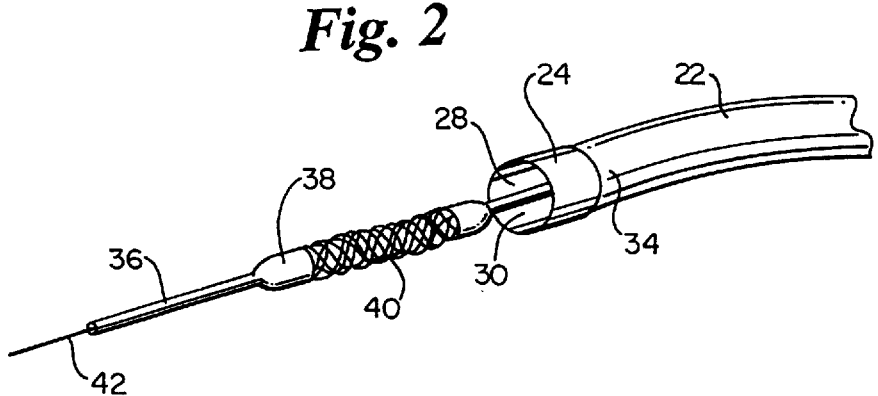
FIG. 2 is a perspective view of the distal portion of the device of the present invention shown with a stent on a balloon catheter extending beyond the distal tip of the present invention.

In FIG. 2, a balloon catheter 36 is shown extending past the distal tip 24 of the catheter 22. More specifically, the balloon catheter 36 is shown with a balloon 38 and a stent 40 which has been positioned around the balloon 38 of balloon catheter 36. As shown in FIG. 2, the stent 40 is in a collapsed configuration and the balloon 38 is deflated. Additionally, a guidewire 42 is shown which can be used, if desired, to assist in the placement of both the device 20 and balloon catheter 36 in a manner that is well known in the pertinent art.

As indicated above in the Background of the Invention, it is an object of the present invention to retrieve the stent 40 from the vessel of a patient (not shown) when the delivery or placement of the stent 40 in the vessel has been unsuccessful. Unsuccessful delivery of the stent 40 can always be detected while the stent 40 remains in its collapsed configuration (shown in FIG. 2). If unsuccessful, it is desirable that device 20 be able to retrieve stent 40. In accordance with the present invention, this retrieval is accomplished by having the distal tip 24 of device 20 grip onto the stent 40 in a manner as substantially shown in FIG. 3.

Figure 4:
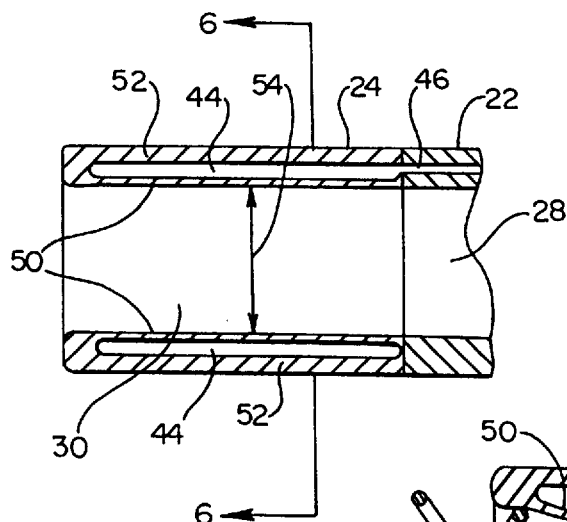
FIG. 4 is a cross sectional view of the distal tip of the present invention with stent and balloon catheter removal as would be seen along the line 4—4 in FIG. 1.

The structural aspects of distal tip 24 which allow the device 20 to grip stent 40 will, perhaps, be best understood by now referring to FIG. 4. There it will be seen that distal tip 24 is formed with a chamber 44 which is in fluid communication with an inflation lumen 46 that is formed in catheter 22. Further, as indicated in FIG. 1, it is to be appreciated that the inflation lumen 46 is connected directly into fluid communication with the inflation unit 26 via a line 48 in any manner well known in the art. As stated above, distal tip 24 is made of a relatively elastic material which is capable of being stretched when subjected to pressure.

Figure 5:
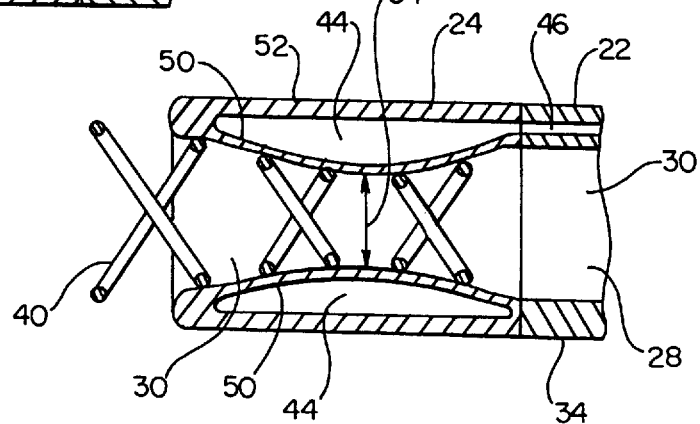
FIG. 5 is a cross sectional view of the distal tip of the present invention as shown in FIG. 4 with the distal tip gripping a stent as shown in FIG. 3.
Figure 6:
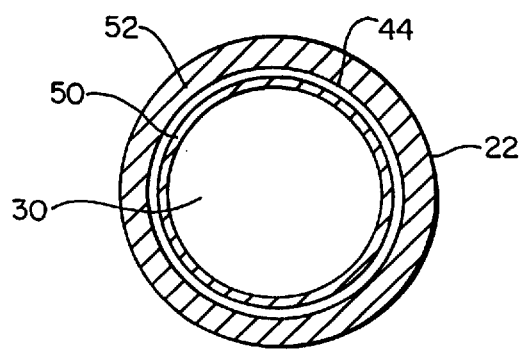
FIG. 6 is a cross sectional view of the distal tip of the present invention as seen along the line 6—6 in FIG. 1.

Still referring to FIG. 4, it will be seen that the chamber 44 is established and located between an inner wall 50 and an outer wall 52. Further, the inner wall 50 surrounds that portion of passageway 30 which extends through distal tip 24. Importantly, this inner wall 50 is more flexible, and thus more susceptible to stretching, than is the outer wall 52. This is so because, as shown, inner wall 50 is thinner than is the outer wall 52. Consequently, when inflation unit 26 is activated to increase fluid pressure in chamber 44, the inner wall 50 will distend in a manner substantially as shown in FIG. 5. This distention of inner wall 50 then decreases the diameter of passageway 30 in distal tip 24 from a distance 54 (shown in FIG. 4) to a distance 54' (shown in FIG. 5). With this decrease in the distance 54, distal tip 24 is capable of griping onto the portion of stent 40 that is then located in passageway 30 of distal tip 24. For a more complete appreciation of the structure of device 20 which forms chamber 44 in distal tip 24, refer to FIG. 6. There it will be noted that chamber 44 completely surrounds the passageway 30. Thus, a distention of distal tip 24 will result in a gripping of stent 40 from all radial directions.

Figure 7:
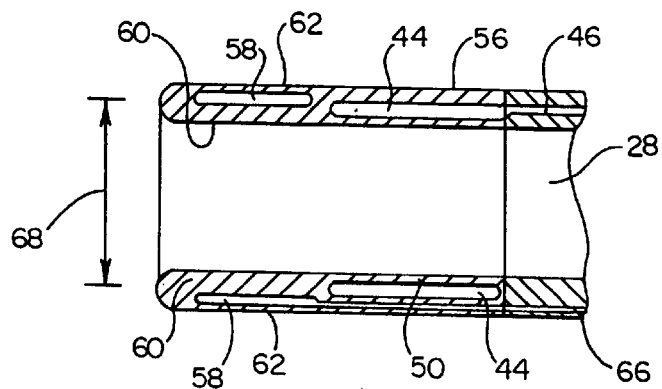
FIG. 7 is a cross sectional view of an alternate embodiment of the distal tip of the present invention as would be seen along the line 4—4 in FIG. 1.

In an alternate embodiment of the present invention, the catheter 22 is modified to include a distal tip 56 which includes a compartment 58. FIG. 7 is illustrative of this alternate embodiment and best shows the structural modifications which distinguish the distal tip 56 from the distal tip 24 shown in FIG. 4. As shown in FIG. 7, the compartment 58 of distal tip 56 is located distally from the chamber 44 and is, in all essential respects, the same as the chamber 44 previously disclosed for distal tip 24. The main difference between the two being a reversal in the radial location of the thicker and thinner members.

Figure 8:
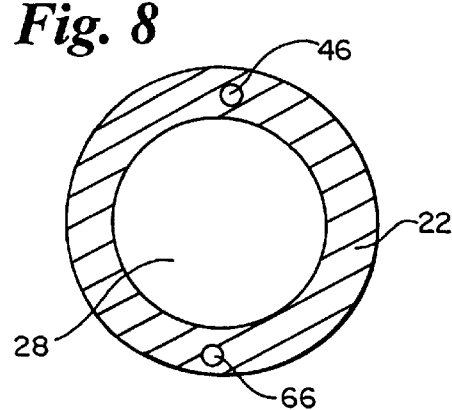
FIG. 8 is a cross sectional view of the catheter of the present invention, which can be used with the alternate embodiment of the distal tip, as seen along the line 8—8 in FIG. 1.

In FIG. 7 it will be seen that the compartment 58 is formed by an inner panel 60 which is radially inside and radially distanced from an outer panel 62. Also seen in FIG. 7 is the fact that the outer panel 62 is thinner, and thus more susceptible to stretching, than is the inner panel 60. Further, it can be appreciated by cross referencing FIG. 7 with FIG. 1 that the inflation unit 26 is connected via line 64 with an inflation lumen 66 which places the inflation unit 26 in fluid communication with the compartment 58. As is to be appreciated by reference to FIG. 8, both inflation lumens 46 and 66 run the length of catheter 22.

Figure 9:
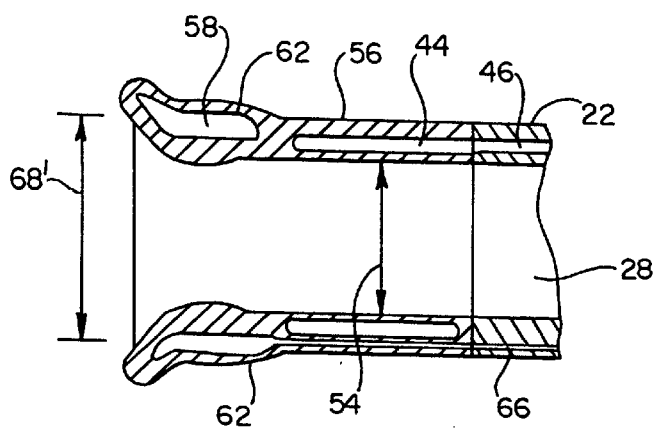
FIG. 9 is a cross sectional view of the distal tip of the alternate embodiment of the present invention as shown in FIG. 7 with the compartment of the distal tip distended.
Figure 10:
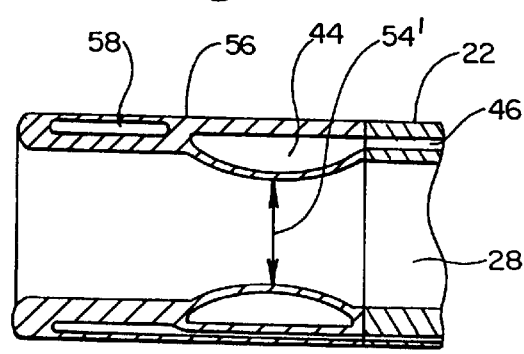
FIG. 10 is a cross sectional view of the distal tip of the alternate embodiment of the present invention as shown in FIG. 7 with the chamber of the distal tip distended.

FIG. 9 indicates that when the compartment 58 is inflated by the inflation unit 26, the outer panel 62 tends to expand relative to inner panel 60. This differential expansion between outer panel 62 and inner panel 60 which occurs upon inflation of compartment 58 causes the outer panel 62 of distal tip 56 to distend. Importantly, this distention of outer panel 62 also prompts the distal tip 56 to flare in a manner that causes the distance 68 (shown in FIG. 7) to increase to the distance 68' (shown in FIG. 9). As will be appreciated by cross referencing FIGS. 9 and 10, the compartment 58 of distal tip 56 can be inflated separately from the inflation of chamber 44. On the other hand, it will also be appreciated that both the compartment 58 and the chamber 44 of distal tip 56 can be simultaneously inflated.

Figure 3:
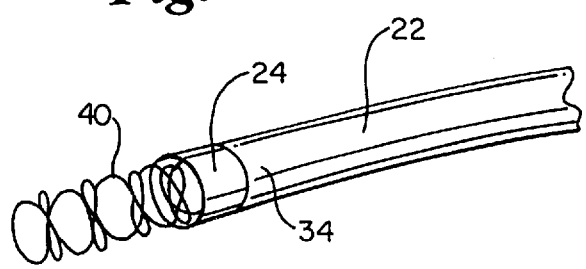
FIG. 3 is a perspective view of the present invention, as shown in FIG. 2, with the device engaged onto a stent for withdrawal or retrieval of the stent from the vessel of a patient.

To consider the operation of the preferred embodiment of the device 20 of the present invention, it is to be assumed that the stent 40 has somehow been unsuccessfully positioned into the vessel of a patient. To retrieve the misplaced stent 40, the stent is withdrawn until contact is made with the distal tip 24 of catheter 22, and until the distal tip 24 surrounds a portion of the stent 40, such as is shown in FIG. 3. Inflation unit 26 is then activated to increase fluid pressure in chamber 44. This increase in pressure causes distal tip 24 to distend and to grip onto the stent 40, such as is shown in FIG. 4. While distal tip 24 grips the stent 40, the catheter 22 with gripped stent 40 can be withdrawn from the patient and thereby retrieved without dislodgement.

In the operation of the alternate embodiment of the present invention, the distal tip 58 of device 20 is advanced into contact with the stent 40 much the same is disclosed above for the preferred embodiment. Upon contact with stent 40, however, in order to facilitate engagement of the device 20 with stent 40, the extreme distal end portion of distal tip 58 can be flared by inflating compartment 58. This flare is intended to allow further unhindered advancement of the distal tip 58 over the stent 40. Then, as before, if necessary, the chamber 44 is inflated to distend a portion of the tip 58 (see FIG. 10) and grip onto the stent 40. Again, the stent 40 is retrieved with the device 20.

While the particular device for retrieving a stent from the vessel of a patient as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A device for placement and removal of a stent from a vessel, comprising:

a stent delivery catheter having a proximal end and a distal end, the distal end configured to carry a stent into the vessel;

a catheter shaft defining a lumen therethrough, the shaft having a proximal end and a distal end, the stent delivery catheter being disposed within the lumen;

a distal tip disposed at the distal end of the shaft, a portion of the lumen extending therethrough, the distal tip including a compartment; and inflation means connected in fluid communication with the compartment for enlarging the compartment and distending the distal tip to increase a transverse inside dimension of the catheter shaft at the distal tip of the catheter shaft to guide the stent into the lumen.

2. A device as recited in claim 1 wherein said catheter is formed with an inflation lumen, said inflation lumen being in fluid communication with said compartment and said inflation means.

3. A device as recited in claim 2 wherein said inflation means includes a fluid pump.

4. A device as recited in claim 1 wherein said distal tip includes an outer wall and an inner wall with said compartment therebetween.

5. A device as recited in claim 1 wherein said distal tip is formed with a chamber, said chamber being located proximally of said compartment, and wherein said inflation means is connected in fluid communication with said chamber to decrease the transverse cross sectional area of the lumen proximate the distal end to grasp the stent.

6. A device as recited in claim 1 wherein said distal tip is made of latex.

7. A device as recited in claim 1 wherein said catheter is made of a teflon duralin material.

8. A method for retrieving a stent from a vessel of a patient comprising the steps of:

providing a stent delivery catheter in said vessel, said stent having a proximal end and a distal end, and said stent being disposed proximate said distal end;

advancing a device into the vessel over said delivery catheter, said device including a stent removal catheter formed with a central lumen defining a passageway for receiving said stent and said delivery catheter, a distal tip attached to said stent removal catheter to surround a portion of said passageway, said distal tip being deformable between a first configuration and a second configuration wherein said distal tip is distended to increase an inside transverse dimension of the stent removal catheter;

deforming said distal tip from said first configuration and into said second configuration; and withdrawing at least a portion of said stent into said passageway of said distal tip while said stent delivery catheter is disposed in said central lumen.

9. A method in accordance with claim 8, wherein the device includes a compartment in the distal tip in fluid communication with an inflation means for introducing fluid into the compartment to deform the tip between the first configuration and the second configuration.

10. A method in accordance with claim 8, wherein the device includes a chamber proximate the distal tip and an inflation means in fluid communication with the chamber for expanding the chamber between a first configuration and a second configuration, the second configuration reducing the inside dimension of the stent removal catheter to grasp the stent.

\* \* \* \* \*